United States Patent [19]
Sit et al.

[11] Patent Number: 5,922,735
[45] Date of Patent: Jul. 13, 1999

[54] 4-ARYL-3-HYDROXYQUINOLIN-2-ONE DERIVATIVES AS ION CHANNEL MODULATORS

[75] Inventors: Sing-Yuen Sit, Meriden; Nicholas A. Meanwell, East Hampton, both of Conn.

[73] Assignee: Bristol-Myers Squibb COmpany, Princeton, N.J.

[21] Appl. No.: 09/166,273

[22] Filed: Oct. 5, 1998

Related U.S. Application Data

[62] Division of application No. 08/972,280, Nov. 18, 1997, Pat. No. 5,892,045
[60] Provisional application No. 60/031,105, Nov. 26, 1996.

[51] Int. Cl.$^6$ .................................................. A61K 31/55
[52] U.S. Cl. .......................................... 514/312; 514/826
[58] Field of Search ...................................... 514/312, 826

[56] References Cited

U.S. PATENT DOCUMENTS 5,200,422  4/1993  Olesen et al. .
5,565,483  10/1996  Hewawasam et al. .

FOREIGN PATENT DOCUMENTS 477819  4/1992  European Pat. Off. .
WO 93/08800  5/1993  WIPO .

OTHER PUBLICATIONS

Database Chemical Abstracts on STN, AN 1986:19486, Modammed et al, "Synthesis of 4–substituted–3–hydroxy–2–quinolones and azines" Pharmazie (Jan. 1985), 40(5), 312–14.
Database Chemical Abstracts on STN, AN 1986:184992, Kharchencko, "Antimicrobial activity of mycotoxins", Mikrobiol. Zh. (Kiev) (Jan. 1986), 48(1), 71–7.
Ahmed, F. et al., "Some Features of the Spasmogenic Actions of Acetylcholine and Histamine in Guinea–Pig Isolated Trachealis", *Br. J. Pharmacol.*, 83, pp. 227–233 (1984).
Baró, I. and Escande, D., "A Ca$^{2+}$–activated k$^+$ Current in Guinea–pig Atrial Myocytes", *Pflügers Archiv.*, 414(Suppl. 1), pp. S168–S170 (1989).
Cook, N. S., "The Pharmacology of Potassium Channels and Their Therapeutic Potential", *Trends in Pharmacol. Sciences*, 9, pp. 21–28 (Jan., 1988).
Koh, D.–S., et al. "Effect of the Flavoid Phloretin on Ca$^{2+}$–activated K$^+$ Channels in Myelinated Nerve Fibres of *Xenopus Laevis*", *Neuroscience Lett.* 165, pp. 167–170 (1994).
Laurent, F. et al., "Evaluation of the Relaxant Effects of SCA40, A Novel Charybdotoxin–Sensitive Potassium Channel Opener, in Guinea–Pig Trachealis", *Br. J. Pharmacol.*, 108, pp. 622–626 (1993).
Masoud, M. S., et al, "Spectral Studies on Some 2–Quinolones", *Spectroscopy Letters*, 21 (6), pp. 369–383 (1988).
Masoud, M. S., et al., "Solution Equilibria and Structures of Some 2–Quinolone Iron (III), Cobalt (II), Nickel (II) and Copper (II) Complexes", *Synth. React. Inorg. Met.–Org. Chem.*, 17, (8 & 9), pp. 881–899 (1987).
Mohammed, Y. S., et al, "Synthesis of 4–Substituted – 3–hydroxy–2–quinolones and Azines", *Pharmazie*, 40, pp. 312–314 (1985).
Olesen, S.–P., et al, "Selective Activation of Ca$^{2+}$–dependent K$^+$ channels by Novel Benzimidazolone", *European J. Pharmacol.*, 251, pp. 53–59 (1994).
Quast, U. and Cook, N. S, "Moving Together: K$^+$ Channel Openers and ATP–sensitive K$^+$ Channels", *Trends in Pharmacol. Sciences*, 10, pp. 431–435 Nov., 1989).
Singer, J. J. and Walsh, J. V., "Characterization of Calcium–activated Potassium Channels in Single Smooth Muscle Cells Using the Patch–clamp Technique", *Pflügers Archiv.*, 408, pp. 98–111 (1987).
*The Merck Index*, 11th Edition, p. 1575 (1989).
Walser, A., et al, "Cyclization Products Derived from o–Benzoyl Malonanilates", *J. Org. Chem.*, 38, (3), pp. 449–456 (1973).

*Primary Examiner*—Keith D. MacMillan
*Attorney, Agent, or Firm*—Aldo A. Algieri

[57] ABSTRACT

There is provided novel substituted 4-aryl-3-hydroxyquinolin-2-one derivatives of the formula

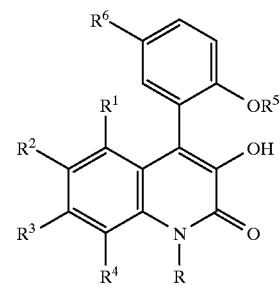

wherein R is hydrogen or methyl;
$R^1$, $R^2$, $R^3$ and $R^4$ each are independently hydrogen, bromo, chloro or trifluoromethyl, and when $R^1$, $R^3$ and $R^4$ are hydrogen, $R^2$ is nitro;
$R^5$ is hydrogen or methyl; and
$R^6$ is bromo or chloro;
or a nontoxic pharmaceutically acceptable salt thereof, which are openers of the large-conductance calcium-activated potassium channels and are useful in the treatment of disorders which are responsive to the opening of the potassium channels.

2 Claims, No Drawings

4-ARYL-3-HYDROXYQUINOLIN-2-ONE DERIVATIVES AS ION CHANNEL MODULATORS

CROSS-REFERENCE TO RELATED APPLICATIONS

This is a divisional application of application U.S. Ser. No. 08/972,280 filed Nov. 18, 1997 now U.S. Pat. No. 5,892,045 which claims the benefit of provisional application, U.S. Ser. No. 60/031,105 filed Nov. 26, 1996.

FIELD OF THE INVENTION

The present invention is directed to novel 4-aryl-3-hydroxyquinolin-2-one derivatives which are modulators of the large-conductance calcium-activated potassium (BK) channels and, therefore, useful in the protection of neuronal cells and diseases arising from dysfunction of cellular membrane polarization and conductance.

BACKGROUND OF THE INVENTION

Potassium channels play a key role in regulation of cell membrane potential and modulation of cell excitability. Potassium channels are largely regulated by voltage, cell metabolism, calcium and receptor mediated processes. [Cook, N. S., *Trends in Pharmacol. Sciences* (1988), 9, 21; and Quast, U., et al, *Trends in Pharmacol. Sciences* (1989), 10, 431]. Calcium-activated potassium ($K_{Ca}$) channels are a diverse group of ion channels that share a dependence on intracellular calcium ions for activity. The activity of $K_{Ca}$ channels is regulated by intracellular [$Ca^{2+}$], membrane potential and phosphorylation. On the basis of their single-channel conductances in symmetrical $K^+$ solutions, $K_{Ca}$ channels are divided into three subclasses: large conductance (BK)>150 pS; intermediate conductance 50–150 pS; small conductance<50 pS. Large-conductance calcium-activated potassium (Maxi-K or BK) channels are present in many excitable cells including neurons, cardiac cells and various types of smooth muscle cells. [Singer, J. et al., *Pflugers Archiv.* (1987) 408, 98; Baro, I., et al., *Pflugers Archiv.* (1989) 414 (Suppl. 1), S168; and Ahmed, F. et al., *Br. J. Pharmacol.* (1984) 83, 227].

Potassium ions play a dominant role in controlling the resting membrane potential in most excitable cells and maintain the transmembrane voltage near the $K^+$ equilibrium potential ($E_k$) of about −90 mV. It has been shown that opening of potassium channels shift the cell membrane potential towards the equilibrium potassium membrane potential ($E_k$), resulting in hyperpolarization of the cell. [Cook, N. S., *Trends in Pharmacol. Sciences* (1988), 9, 21]. Hyperpolarized cells show a reduced response to potentially damaging depolarizing stimuli. BK channels which are regulated by both voltage and intracellular $Ca^{2+}$ act to limit depolarization and calcium entry and may be particularly effective in blocking damaging stimuli. Therefore cell hyperpolarization via opening of BK channels may result in protection of neuronal cells.

A range of synthetic and naturally occurring compounds with BK opening activity have been reported. The avena pyrone extracted from avena sativa-common oats has been identified as a BK channel opener using lipid bi-layer technique [International Patent application WO 93/08800, published May 13, 1993]. 6-Bromo-8-(methylamino) imidazo[1,2-a]pyrazine-2-carbonitrile (SCA-40) has been described as a BK channel opener with very limited electrophysiological experiments [Laurent, F. et al., *Br. J. Pharmacol.* (1993) 108, 622–626]. The flavanoid, Phloretin has been found to increase the open probability of $Ca^{2+}$-activated potassium channels in myelinated nerve fibers of *Xenopus laevis* using outside-out patches [Koh, D- S., et al., *Neuroscience Lett.* (1994) 165, 167–170].

In European patent application EP-477,819 published Jan. 4, 1992 and corresponding U.S. Pat. No. 5,200,422, issued Apr. 6, 1993 to Olesen, et al., a number of benzimidazole derivatives were disclosed as openers of BK channels by using single-channel and whole-cell patch-clamp experiments in aortic smooth muscle cells. Further work was reported by Olesen, et al in *European J. Pharmacol.*, 251, 53–59 (1994).

A number of substituted oxindoles have been disclosed as openers of BK channels by P. Hewawasam, et al, in U.S. Pat. No. 5,565,483, issued Oct. 15, 1996.

A. Walser, et al, *J. Org. Chem.*, 38, 449–456 (1973) disclose a limited number of 3-hydroxyquinolinones as by-products formed during the opening of the epoxide intermediate.

Y. S. Mohammed, et al, *Pharmazie*, 40, 312–314 (1985) discloses a series of 4-substituted-3-hydroxy-2-quinolones as analogues of the natural product viridicatin. The Merck Index, 11th Edition, 1575 (1989) briefly summarizes the references to the antibiotic substance, viridicatin.

M. S. Masoud, et al, in *Spectroscopy Letters*, 21 (6), 369–383 (1988) describe the spectral properties of several 2-quinolones as liquids and in *Synth. React. Inorg. Met.-Org. Chem.*, 17, (8 & 9), 881–899 (1987) describe the equilibria and stability of the 2-quinolones in metallic complexes.

It is the object of the present invention to provide novel compounds that will modulate potassium channels, in particular, large-conductance calcium-activated potassium (BK) channels which will be useful in reducing neuronal damage.

SUMMARY OF THE INVENTION

The present invention provides novel 4-aryl-3-hydroxyquinolin-2-one derivatives having the general formula

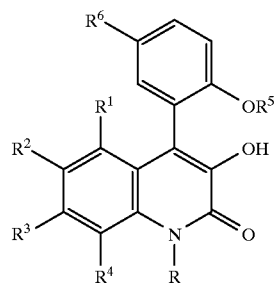

wherein R, $R^1$, $R^2$, $R^3$, $R^4$, $R^5$ and $R^6$ are as defined below, or a non-toxic pharmaceutically acceptable salt thereof which are openers of the large conductance calcium-activated $K^+$ channels also known as Maxi-K or BK channels. The present invention also provides pharmaceutical compositions comprising said quinolin-2-one derivatives and to the method of treatment of disorders sensitive to potassium channel opening activity such as ischemia, convulsions, asthma, irritable bowel syndrome, migraine, traumatic brain injury, and urinary incontinence.

DETAILED DESCRIPTION OF THE INVENTION

The present invention provides novel 4-aryl-3-hydroxyquinolin-2-one derivatives which are potent openers of the high conductance, calcium-activated K⁺-channels (BK channel) and which have the formula

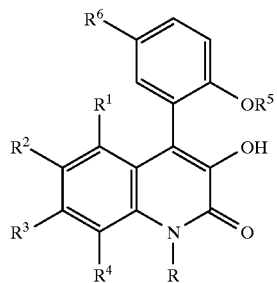

wherein
R is hydrogen or methyl;
$R^1$, $R^2$, $R^3$
and $R^4$ each are independently hydrogen, bromo, chloro or trifluoromethyl, and when $R^1$, $R^3$ and $R^4$ are hydrogen, $R^2$ is nitro;
$R^5$ is hydrogen or methyl; and
$R^6$ is bromo or chloro;
or a nontoxic pharmaceutically acceptable salt thereof.

The present invention also provides a method for the treatment or alleviation of disorders associated with BK channels, especially ischemia, convulsions, asthma, irritable bowel syndrome, migraine, traumatic brain injury, and urinary incontinence, which comprises administering together with a conventional adjuvant, carrier or diluent a therapeutically effective amount of a compound of formula I or a nontoxic pharmaceutically acceptable salt thereof.

The term "nontoxic pharmaceutically acceptable salt" as used herein and in the claims is intended to include nontoxic base addition salts with inorganic bases. Suitable inorganic bases such as alkali and alkaline earth metal bases include metallic cations such as sodium, potassium, magnesium, calcium and the like.

Certain of the compounds of the present invention can exist in unsolvated forms as well as solvated forms including hydrated forms such as monohydrate, dihydrate, hemihydrate, trihydrate, tetrahydrate and the like. The products may be true solvates, while in other cases, the products may merely retain adventitious solvent or be a mixture of solvate plus some adventitious solvent. It should be appreciated by those skilled in the art that solvated forms are equivalent to unsolvated forms and are intended to be encompassed within the scope of the present invention.

In the method of the present invention, the term "therapeutically effective amount" means the total amount of each active component of the method that is sufficient to show a meaningful patient benefit, i.e., healing of acute conditions characterized by openers of large conductance calcium-activated K⁺ channels or increase in the rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases, tissue damage and/or symptoms associated with dysfunction of cellular membrane polarization and conductance.

The compounds of Formula I may be prepared by various procedures such as those illustrated herein in the examples, in the reaction schemes and variations thereof which would be evident to those skilled in the art. The various quinolin-2-one derivatives of Formula I may advantageously be prepared from isatin intermediates which are generally well-known and a general method of preparation is illustrated in Reaction Scheme 1.

In the process for the preparation of isatin intermediates of the Formula III, a number of commonly known and well-established procedures may be employed such as those described by Sandmeyer, T., *Helv. Chim. Acta*, 2, 234 (1919); Stolle, R., *J. Prakt. Chem.*, 105, 137 (1922); and Gassman, P., et al., *J. Org. Chem.*, 42, 1344 (1977). However, a more preferred method for the preparation of isatins of Formula III starting from the appropriately substituted anilines of Formula V is generally described by Hewawasam, P., et al., *Tetrahedron Lett.*, 35, 7303 (1994) and is illustrated in Reaction Scheme 1. This method appears to be insensitive to the electronic nature of substituents bound to the aromatic ring and is characterized by predictable regiochemical control.

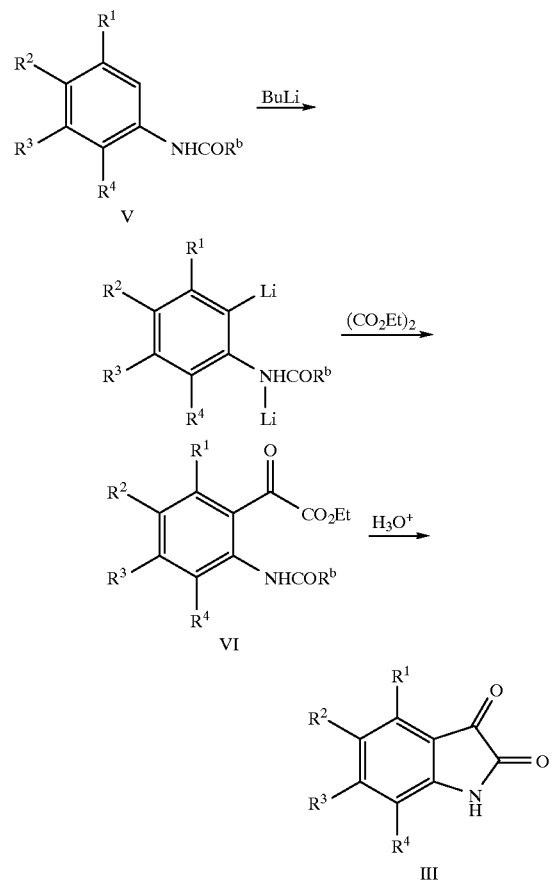

REACTION SCHEME 1

It will be appreciated by those skilled in the art that when the amino group of an aniline compound of Formula V is suitably protected such as with N-pivaloyl and N-(tert-butoxycarbonyl) protecting groups, it can direct metalation to the ortho position. Once the dianions are formed, the reaction with about 1.2 equivalents of diethyl oxalate at low temperatures such as −78° C. may be used to introduce an α-ketoester moiety ortho to the protected amino group of the aniline derivative to produce the compound of Formula VI. Removal of the protecting group followed by spontaneous cyclization will advantageously produce the isatin of Formula Ill. To elaborate further on the process of Reaction Scheme 1, the dianions of N-pivaloylanilines or N-(tert-butoxycarbonyl) anilines are advantageously generated using about 2.2 to 2.4 fold excess of a variety of butyllithium reagents, such as n-butyl-, s-butyl- and t-butyl-lithium reagents in THF at about 0 to −40° C. for 2 to 7 hours.

In a typical procedure, neat dry diethyl oxalate (1.2 equivalents) was added to a solution of the dianion stirred at −78° C. under nitrogen. After being stirred for 30–45 minutes, the reaction was quenched with 1N HCl and diluted with diethyl ether to afford the compound of Formula VI. Although the intermediate α-ketoesters of Formula VI may be purified for purposes of characterization, this step is not necessary and the crude product can be advantageously deprotected to afford the isatins in excellent overall yield. Deprotection of the N-(tert-butoxycarbonyl) or pivaloyl moieties may be carried out using 3N HCl/THF or 12N HCl/DME, respectively, at reflux temperature. Upon evaporation of the volatile solvents, the isatins generally precipitated from the aqueous residue and are isolated by filtration.

Isatins of Formula III, prepared as described in the above Reaction Scheme 1 or by well-known literature procedures, were converted to the 4-aryl-3-hydroxyquinolin-2-ones of Formulas I*a* and I*b* as shown in Reaction Scheme 2.

In the process for the preparation of compounds of Formula I*a*, the hydrazone of Formula IV is condensed with the appropriate isatin of Formula IIll to produce a mixture of quinolinone regioisomers of Formula I*a* and II. The hydrozones of Formula IV are advantageously prepared from the corresponding readily available substituted benzaldehydes. The condensation reaction is conducted in a $C_{1-4}$ alcohol solvent such as methanol, ethanol and 2-propanol in the presence of base derived from an earth metal salt of lower alkynols such as sodium methoxide. The reaction is advantageously conducted above room temperature and preferably at about 65–100° C. for about 3 to 12 hours. The resulting mixture of isomers of Formula I*a* and II are suspended and heated in ethyl acetate and filtered. Usually the less soluble and in most instances the undesirable quinolinone regioisomer of Formula II is removed by filtration. The separation and the successful removal of the undesired isomer was ascertained by $^1$H NMR. In most cases, the separation and removal of the undesired isomer was complete. However, if the separation was not complete, it is desirable to re-suspend the solid mixture in ethyl acetate to remove insoluables. This process can be repeated several times, if necessary, until a single isomer is obtained.

Alternatively, the preparation of quinolinones of the Formula I*a* may be carried out from the corresponding isatin of Formula III wherein Ra is —$CH_2OCH_3$ or $CH_3$ and the hydrazone of Formula IV. It has been found that the use of a methoxymethyl group as a protecting (blocking) group for Ra in the condensation reaction of the process illustrated in Reaction Scheme 2 will advantageously produce a much higher amount of the desired regioisomer of Formula I*a*.

Demethylation of the methyl ether moiety of the compound of Formula la with $BBr_3$ in $CH_2Cl_2$ under carefully controlled conditions from −78 to 0° C. afforded the desired phenols of Formula I*b*. The reaction should preferably not be warmed above 0° C. After completion of the demethylation, quenching of the reaction afforded the 4-aryl-3-hydroxyquinolin-2-ones of Formula I*b*.

REACTION SCHEME 2

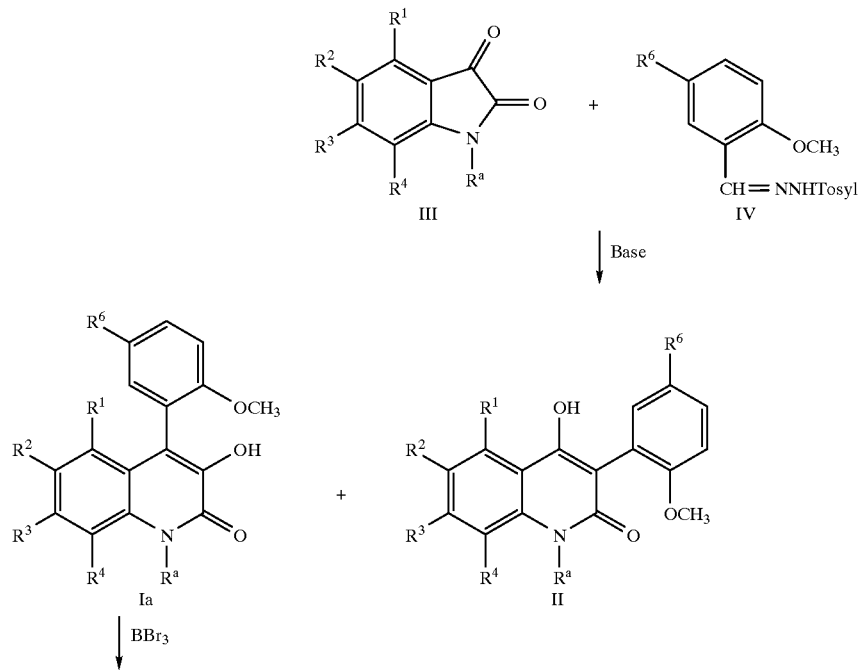

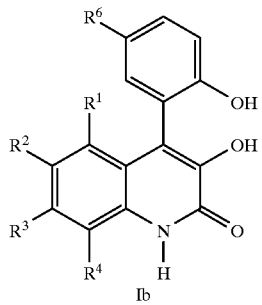

In addition to the differences observed in the proton NMR spectrum for the regioisomers of Formula I*a* and II, the absolute structure of the desired regioisomeric compound of Formula I*a* and I*b* was verified and confirmed by single crystal x-ray analysis. In general, the experimental $^1$H NMR spectra in DMSO-$d_6$ of the compound of formula 1a and 1b exhibited certain characteristic chemical shift peaks in the proton spectrum which distinguished these products from the undesired regioisomer of formula II. The chemical shift for the 3-OH peak was observed at about 9.5–9.8 ppm and the NH peak was observed at about 12.2–12.6 ppm while the regioisomer of formula II generally exhibited chemical shifts for the 4-OH peak at about 10–10.5 ppm and the NH peak at about 11.5–11.8 ppm.

In a preferred embodiment of the invention the compounds of Formula I have the formula

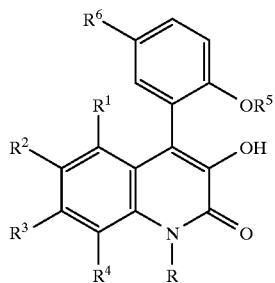

wherein R is hydrogen, $R^1$, $R^2$, $R^3$ and $R^4$ each are independently hydrogen, bromo, chloro, or trifluoromethyl, and when $R^1$, $R^3$ and $R^4$ are hydrogen, $R^2$ is nitro; or a nontoxic pharmaceutically acceptable salt thereof.

In another aspect, this invention provides a method for the treatment of or protection from disorders which are mediated by opening of the large conductance calcium-activated $K^+$ channels (BK channels) in a mammal in need thereof, which comprises administering to said mammal a therapeutically effective amount of a compound of Formula I or a nontoxic pharmaceutically acceptable salt thereof. Preferably, the compounds of Formula I are useful in the treatment of ischemia, convulsions, asthma, irritable bowel syndrome, migraine, traumatic brain injury, and urinary incontinence and other disorders sensitive to BK channel activating activity.

In still another aspect, this invention provides pharmaceutical compositions comprising at least one compound of Formula I in combination with a pharmaceutical adjuvant, carrier or diluent.

Biological Activity

Potassium ($K^+$) channels are structurally and functionally diverse families of $K^+$-selective channel proteins which are ubiquitous in cells, indicating their central importance in regulating a number of key cell functions [Rudy, B., *Neuroscience*, 25: 729–749 (1988)]. While widely distributed as a class, $K^+$ channels are differentially distributed as individual members of this class or as families. [Gehlert, D. R., et al., *Neuroscience*, 52: 191–205 (1993)]. In general, activation of $K^+$ channels in cells, and particularly in excitable cells such as neurons and muscle cells, leads to hyperpolarization of the cell membrane, or in the case of depolarized cells, to repolarization. In addition to acting as an endogenous membrane voltage clamp, $K^+$ channels can respond to important cellular events such as changes in the intracellular concentration of ATP or the intracellular concentration of calcium ($Ca^{2+}$). The central role of $K^+$ channels in regulating numerous cell functions makes them particularly important targets for therapeutic development. [Cook, N. S., Potassium channels: Structure, classification, function and therapeutic potential. Ellis Horwood, Chinchester (1990)]. One class of K+ channels, the large-conductance $Ca^{2+}$-activated $K^+$ channels (Maxi-K or BK channels), is regulated by transmembrane voltage, intracellular $Ca^{2+}$, and a variety of other factors such as the phosphorylation state of the channel protein. [Latorre, R., et al., *Ann. Rev. Pysiol.*, 51: 385–399 (1989)]. The large, single channel-conductance (generally>150 pS) and high degree of specificity for $K^+$ of BK channels indicates that small numbers of channels could profoundly affect membrane conductance and cell excitability. Additionally, the increase in open probability with increasing intracellular $Ca^{2+}$ indicates involvement of BK channels in the modulation of $Ca^{2+}$-dependent phenomena such as secretion and muscular contraction. [Asano, M., et al., *J. Pharmacol. Exp. Ther.*, 267: 1277–1285 (1993)].

Openers of BK channels exert their cellular effects by increasing the open probability of these channels [McKay, M. C., et al., *J. Neurophysiol.*, 71: 1873–1882 (1994); and Olesen, S.-P., *Exp. Opin. Invest. Drugs*, 3: 1181–1188 (1994)]. This increase in the opening of individual BK channels collectively results in the hyperpolarization of cell membranes, particularly in depolarized cells, produced by significant increases in whole-cell BK-mediated conductance.

The ability of compounds described in the present invention to open BK channels and increase whole-cell outward ($K^+$) BK-mediated currents was assessed under voltage-clamp conditions by determining their ability to increase cloned mammalian (mSlo or hSlo) BK - mediated outward current heterologously expressed in Xenopus oocytes [Butler, A., et al., *Science*, 261: 221–224 (1993); and Dworetzky, S. I., et al., *Mol. Brain Res.*, 27: 189–193 (1994)]. The two BK constructs employed represent nearly structurally identical homologous proteins, and have proven to be pharmacologically identical in our tests. To isolate BK current from native (background, non-BK) current, the specific and potent BK channel-blocking toxin iberiotoxin (IBTX) [Galvez, A., et al., *J. Biol. Chem.*, 265: 11083–11090 (1990)] was employed at a supramaximal concentration (50 nM). The relative contribution of BK channels current to total outward current was determined by subtraction of the current remaining in the presence of IBTX (non-BK current) from the current profiles obtained in all other experimental conditions (control, drug, and wash). It was determined that at the tested concentration the compounds profiled did not effect non-BK native currents in the oocytes. All compounds were tested in at least 5 oocytes and are reported at the single concentration of 20 $\mu$M; the effect of the selected compounds of Formula I on BK current was expressed as the percent of control IBTX-sensitive current and is listed in Table I. Recordings were accomplished using standard two-electrode voltage clamp techniques [Stuhmer, W., et al., *Methods in Enzymology*, Vol. 207: 319–339 (1992)]; voltage-clamp protocols consisted of 500–750 ms duration step depolarizations from a holding potential of −60 mV to +140 mV in 20 mV steps. The experimental media (modified Barth's solution) consisted of (in mM): NaCl (88), NaHCO3 (2.4), KCl (1.0), HEPES (10), MgSO4 (0.82), Ca(NO3)2 (0.33), CaCl2 (0.41); pH 7.5.

TABLE I

Effect of Selected Compounds on BK Channels

| Example No. | BK Current* |
|---|---|
| 2 | ++ |
| 3 | + |
| 4 | ++ |
| 5 | + |
| 6 | + |
| 7 | + |
| 8 | + |
| 9 | ++ |
| 10 | ++ |
| 11 | ++ |
| 12 | ++ |
| 13 | + |
| 14 | + |
| 15 | ++ |
| 16 | ++ |
| 17 | ++ |
| 18 | ++ |
| 19 | ++ |
| 20 | ++ |
| 21 | + |

*at 20 $\mu$M expressed as percent of controls
+ = 100–150%
++ = >150%

The results of the above biological test demonstrates that the compounds of the instant invention are potent openers of the large-conductance calcium-activated K$^+$ channels (Maxi-K or BK channels). Thus, the compounds of the present invention are useful for the treatment of human disorders arising from dysfunction of cellular membrane polarization and conductance and, preferably, are indicated for the treatment of ischemia, convulsions, asthma, irritable bowel syndrome, migraine, traumatic brain injury, and urinary incontinence and other disorders sensitive to BK channel activating activity.

In another embodiment, this invention includes pharmaceutical compositions comprising at least one compound of Formula I in combination with a pharmaceutical adjuvant, carrier or diluent.

In still another embodiment, this invention relates to a method of treatment or prevention of disorders responsive to opening of potassium channels in a mammal in need thereof, which comprises administering to said mammal a therapeutically effective amount of a compound of Formula I or a nontoxic pharmaceutically acceptable salt thereof.

Antibiotic Activity

The in vitro antibacterial activity of a representative number of compounds from the present invention were determined by the two-fold agar dilution method. The activity against the following test organisms were evaluated.

| | |
|---|---|
| *Staphylococcus aureus*/Pen. − | A9537 |
| *Staphylococcus aureus*/Pen. + | A9606 |
| *Staphylococcus epidermidis* | A24548 |
| *Micrococcus luteus* | A9852 |
| *Micrococcus luteus* | A21349 |
| *Bacillus subtilis* | A9506A |

The results using representative compounds of Examples 2, 3, 4, 6, 8, 9, 10, 11 and 12 exhibited fairly good inhibitory activity with MIC values in the range of 0.5 to 32 $\mu$g/ml and mostly in the 1 to 2 $\mu$g/ml level of activity against the gram-positive test organisms.

The novel quinolinones of general Formula I or the pharmaceutically acceptable salts thereof, are active against various gram-positive bacteria and they may be used, for example, as animal feed additives for promotion of growth, as preservatives in food, as bactericides in industrial applications, for example in waterbased paint and in the white water of paper mills to inhibit the growth of harmful bacteria and as disinfectants for destroying or inhibiting the growth of harmful bacteria on medical and dental equipment. They are also useful, however, in the treatment of infectious disease in animals caused by gram-positive bacteria.

In respect to pharmaceutical compositions containing the antibiotic herein, carrier and other ingredients should be such as not to diminish the therapeutic effects of the antibiotic. Suitable dosage forms will comprise an amount effective to inhibit the growth of the bacteria causing the condition of infection and will depend on the age and weight of the mammalian species being treated, the route of administration, and the type and severity of the infectious condition being treated and other factors readily evaluated by the physician or veterinarian in attendance.

For therapeutic use, the pharmacologically active compounds of Formula I will normally be administered as a pharmaceutical composition comprising as the (or an) essential active ingredient at least one such compound in association with a solid or liquid pharmaceutically acceptable carrier and, optionally, with pharmaceutically acceptable adjutants and excipients employing standard and conventional techniques.

The pharmaceutical compositions include suitable dosage forms for oral, parenteral (including subcutaneous, intramuscular, intradermal and intravenous) bronchial or nasal administration. Thus, if a solid carrier is used, the preparation may be tableted, placed in a hard gelatin capsule in powder or pellet form, or in the form of a troche or lozenge. The solid carrier may contain conventional excipients such as binding agents, fillers, tableting lubricants, disintegrants, wetting agents and the like. The tablet may, if desired, be film coated by conventional techniques. If a liquid carrier is employed, the preparation may be in the form of a syrup, emulsion, soft gelatin capsule, sterile vehicle for injection, an aqueous or non-aqueous liquid suspension, or may be a dry product for reconstitution with water or other suitable vehicle before use. Liquid preparations may contain conventional additives such as suspending agents, emulsifying agents, wetting agents, non-aqueous vehicle (including edible oils), preservatives, as well as flavoring and/or coloring agents. For parenteral administration, a vehicle normally will comprise sterile water, at least in large part, although saline solutions, glucose solutions and like may be utilized. Injectable suspensions also may be used, in which case conventional suspending agents may be employed. Conventional preservatives, buffering agents and the like also may be added to the parenteral dosage forms. Particularly useful is the administration of a compound of Formula I directly in parenteral formulations. The pharmaceutical compositions are prepared by conventional techniques appropriate to the desired preparation containing appropriate amounts of the active ingredient, that is, the compound of Formula I according to the invention. See, for example, *Remington's Pharmaceutical Sciences,* Mack Publishing Company, Easton, Pa., 17th edition, 1985.

The dosage of the compounds of Formula I to achieve a therapeutic effect will depend not only on such factors as the age, weight and sex of the patient and mode of administration, but also on the degree of potassium channel activating activity desired and the potency of the particular compound being utilized for the particular disorder of disease concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

A suitable dose of a compound of Formula I or pharmaceutical composition thereof for a mammal, including man, suffering from, or likely to suffer from any condition as described herein is an amount of active ingredient from about 0.1 μg/kg to 100 mg/kg body weight. For parenteral administration, the dose may be in the range of 1 μg/kg to 10 mg/kg body weight for intravenous administration The active ingredient will preferably be administered in equal doses from one to four times a day. However, usually a small dosage is administered, and the dosage is gradually increased until the optimal dosage for the host under treatment is determined. A suitable dose for the treatment of infectious disease in humans will preferably range from about 100 mg to about 1,000 mg of the active ingredient for a 70 kg adult, depending on the nature of the infection and the frequency and route of administration inter alia.

However, it will be understood that the amount of the compound actually administered will be determined by a physician, in the light of the relevant circumstances including the condition to be treated, the choice of compound of be administered, the chosen route of administration, the age, weight, and response of the individual patient, and the severity of the patient's symptoms.

The following examples are given by way of illustration and are not to be construed as limiting the invention in any way inasmuch as many variations of the invention are possible within the spirit of the invention.

DESCRIPTION OF SPECIFIC EMBODIMENTS

In the following examples, all temperatures are given in degrees Centigrade. Melting points were recorded on a Gallenkamp capillary melting point apparatus are uncorrected. Proton magnetic resonance ($^1$H NMR) and carbon magnetic resonance ($^{13}$C NMR) spectra were recorded on a Bruker AC 300 spectrometer. All spectra are determined in the solvents indicated and chemical shifts are reported in δ units downfield from the internal standard tetramethylsilane (TMS) and interproton coupling constants are reported in Hertz (Hz). Splitting patterns are designated as follows: s, singlet; d, doublet; t, triplet; q, quartet; m, multiplet; br, broad peak; dd, doublet of doublet; bd, broad doublet; dt, doublet of triplet; bs, broad singlet; dq, doublet of quartet. Infrared (IR) spectra using potassium bromide (KBr) were determined on a Perkin Elmer 781 spectrometer from 4000 cm$^{-1}$ to 400 cm$^{-1}$, calibrated to 1601 cm$^{-1}$ absorption of a polystyrene film and reported in reciprocal centimeters (cm$^{-1}$). Ultraviolet spectra were determined by Robertson Microlit Laboratories, Inc. in the solvents indicated. Low resolution mass spectra (MS) and the apparent molecular (MH$^+$) was determined on a Finnigan TSQ 7000. The element analysis are reported as percent by weight.

The following procedures Nos.1–3 illustrate representative procedures for the preparation of intermediates and methods for the preparation of products according to this invention. It should also be evident to those skilled in the art that appropriate substitution of both the materials and methods disclosed herein will produce the examples illustrated below and those encompassed by the scope of this invention.

PROCEDURE 1

General Method for Compounds of Formula III wherein

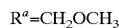

Sodium hydride (850 mg, 60% in mineral oil, 22 mmoles) was rinsed with hexanes (2×5 mL), then DMF (25 mL) was added and the temperature of the suspension was kept at 0–5° C. Isatin reagent of formula III wherein R$^a$=H (20 mmoles) was added into the NaH/DMF suspension in small portions and the resulting dark solution was stirred for 20 minutes. Bromomethyl methyl ether (22 mmoles, 1.1 eq.) was added via a plastic syringe in one portion and the reaction mixture was allowed to stir at room temperature for 16 hours. The crude mixture was poured into water (250 mL), and precipitated product was collected by filtration, washed and dried to give a compound of formula III wherein R$^a$=CH$_2$OCH$_3$.

PROCEDURE 2

General Method for Preparation of Compounds of Formula I*a*

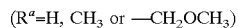

A mixture of isatin of formula III (30 mmol), the compound of formula IV (30 mmol) and NaOMe (90 mL of 1.0 M solution in MeOH, 3 equiv.) in MeOH (150 mL) was heated at reflux for 3–12 hours. When TLC indicated complete conversion, the reaction mixture was cooled to room temperature and added to a 0.5N HCl solution (500 mL) with stirring. The product which precipitated out from the acidified mixture was collected by filtration, washed with water (3×50 mL) and dried under reduced pressure to give a mixture of compounds of formula I*a* and II. The solid mixture was suspended in AcOEt (100 mL) and heated a reflux for about 20 minutes. After cooling to room temperature, the mixture was filtered to remove the undesirable product of formula II. The filtrate was evaporated to dryness and the residue was suspended and stirred in a mixed solvent (100 mL) of AcOEt and hexane (1:4) for about 10 minutes, filtered and dried to produce the compounds of formula I*a*. In some mixtures when the ratio of the desired compound of formula I*a* is high, filtration of the AcOEt suspension will yield the desired product of formula I*a*. In other cases, the compound of formula I*a* can be obtained by flash column chromatography (silica gel, AcOEt/Hexane: 10–30%) of the mixture.

PROCEDURE 3
General Method for Preparation of Compounds of Formula Ib

To a suspension of 6 mmol of methyl ether of formula Ia in methylene chloride was added 30 mL of a solution of BBr$_3$ (1.0M in CH$_2$Cl$_2$, 5.0 equiv.) at −78° C. where upon the reaction became homogenous. The solution was stirred at −78° C. for about 3 hours, the bath was removed and stirring was continued for an additional 20 hours at room temperature. Water (0.5 mL) was added and the reaction was stirred for 10 minutes. The solvents were removed in vacuo to give a solid residue which was suspended in 100 mL of water, sonicated for 5–10 minutes, then stirred for 10 minutes, filtered, washed with water (3 x 30 mL) and dried to produce a compound of formula Ib in nearly quantitative yield.

EXAMPLE 1
5.7-Dichloro-4-(5-chloro-2-methoxyphenyl)-3-hydroxy-2(1 H)-quinolinone and its regioisomer 5.7-dichloro-3-(5-chloro-2-methoxyphenyl)-4-hydroxy-2(1 H)-guinolinone A mixture of 4,6-dichloro-1H-indol-2,3-dione (6.48 g, 0.03 mol), 5-chloro-2-methoxy-[N-(4-methylphenyl) hydrazonomethyl]phenyl (10.65 g, 0.0315 mol, 1.05 eq.) and NaOMe (90 mL of 1.0M solution in methanol) in methanol (150 mL) was heated at reflux temperature for 3 hours. The reaction mixture was cooled and the solid was collected by filtration and washed with methanol (3×10 mL). The solid was suspended in 0.5N HCl solution (500 mL), stirred for 20 minutes then filtered, washed with water (3×50 mL) and dried to yield 2.76 g of the desired isomer 5,7-dichloro-4-(5-chloro-2-methoxyphenyl)-3-hydroxy-2(1 H)-quinolinone.

$^1$H NMR (300 MHz, DMSO-d$_6$) δ: 7.39 (dd, 1 H, J=2.7, 8.8 Hz), 7.36, (1H, d, J=2.2 Hz), 7.23 (1H, d, J=2.2 Hz), 7.15 (1H, d, J=2.2 Hz), 7.02 (1H, d, J=8.9 Hz), 3.64 (3H, s), 12.53 (1H, bs), 9.79 (1H, bs).
$^{13}$C NMR (75 MHz, DMSO-d$_6$) δ: 157.2, 156.0, 145.4, 135.4, 130.2, 130.0, 130.0, 128.8, 126.3, 124.5, 123.6, 118.5, 116.6, 114.4, 112.2, 55.7.
UV(abs. ethanol at 5.2×10$^{-4}$ g/100 mL) λ$_{max}$: 232 (1107), 336 (299), 288 (292), 322 (289) and 310 (221);
MS (DCl):370 (MH$^+$);
IR (KBr, cm$^{-1}$): 3500-2400, 1665, 1300-1200 and 1020.
Anal. calcd. for C$_{16}$H$_{10}$Cl$_3$NO$_3$: C, 51.85; H, 2.72; N, 3.78.
Found: C, 51.89; H, 2.81; N, 3.74.

The filtrate from the above reaction mixture was added to 0.5N HCl solution (1500 mL) with stirring. The product which precipitated from the acidified mixture was collected by filtration and dried to yield 8.11 g of a mixture (6:1) of the regioisomer 5,7-dichloro-3-(5-chloro-2-methoxyphenyl)-4-hydroxy-2(1H)-quinolinone and some of the desired product. A sample of the purified regioisomer had the following characteristics:
$^1$H NMR (300 MHz, DMSO-d$_6$) δ:11.70 (1H, s), 10.08 (1H, s), 7.37 (1H, dd, J=2.7, 8.9 Hz), 7.29 (2H, d, J=1.6 Hz), 7.13 (1 H, d, J=2.6 Hz), 7.05 (1H, d, J=8.9Hz),3.68 (3H,s);
$^{13}$C NMR (75 MHz, DMSO-d$_6$) δ:156.9, 141.2, 134.3, 132.2, 131.6, 128.9, 124.1, 123.6, 113.8, 113.1, 55.7;
UV(abs. ethanol at 4.8×10$^{-4}$ g/100 mL) λ$_{max}$:234 (1480), 296 (373) and 326 (300) nm;
MS (DCl): 370 (MH$^+$);
IR (KBr, cm$^{-1}$): 3500-2500,1660 and 1250.

Anal. calcd. for C$_{16}$H$_{10}$Cl$_3$NO$_3$: C, 51.85; H, 2.72; N, 3.78.
Found: C, 52.01; H, 2.76; N, 3.80.

EXAMPLE 2
5.7-Dichloro-4-(5-chloro-2-hydroxyphenyl)-3-hydroxy-2(1 H)-quinolinone To a suspension of 5,7-dichloro-4-(5-chloro-2-methoxyphenyl)-3-hydroxy-2(1H)-quinolinone (2.22 g, 6.0 mmol) [prepared in Example 1] in methylene chloride was added BBr$_3$ (30 mL, 1.0M solution in methylene chloride, 5.0 equiv.) at −78° C. and the suspension became a clear solution. The solution was stirred under an argon atmosphere at −78° C. for 3 hours then at room temperature for an additional 20 hours. Distilled water (0.5 mL) was added dropwise and stirring continued for 10 minutes. The reaction mixture was evaporated under vacuum and the solid residue was suspended in water (100 mL), sonicated for 5 minutes then stirred for 10 minutes, filtered, washed with water (3×30 mL) and dried to yield 2.15 g (≈100%) of the title compound as a white solid: mp=297–299° C.;

Anal. calcd. for C$_{15}$H$_8$NO$_3$Cl$_3$: C, 48.56; H, 2.61; N, 3.78.
Found: C, 48.64; H, 2.52; N, 3.74.
IR (KBr, cm$^{-1}$): 3600-2000, 1660 and 1250;
UV(abs. ethanol at 5.2×10$^{-4}$ g/100 mL) λ$_{max}$: 232 (1066), 336 (314), 322 (304), 290 (299) and 684 (3.5).
$^1$H NMR (300 MHz, DMSO-d$_6$) δ:12.50, 9.62, 7.35 (1H, d, J=2.2 Hz), 7.22 (1H, d, J=2.4 Hz),7.19 (1H, dd, J=2.7; 8.7 Hz),7.05 (1H, d, J=2.7 Hz), 6.81 (1H, d, J=8.7 Hz);
$^{13}$C NMR (75 MHz, DMSO-d$_6$) δ:157.39, 154.14, 145.53, 135.47, 130.17, 129.78, 128.50, 124.55, 124.79, 121.79, 118.74, 116.87, 116.32, 114.25.

A sample of the title compound was crystallized from EtOAc/H$_2$O to yield colorless rod crystals. The structure and solid state conformation assigned to the title compound was confirmed by single crystal x-ray analysis. The dihedral angle between the plane of the quinoline and the plane of the phenyl substitutent is 100.23(6)°.

EXAMPLES 3–18

Following the general procedures Nos. 2 and 3, and the representative Examples 1 and 2, the following 4-aryl-3-hydroxyquinolin-2-one products are made using the appropriate intermediates of formulas III and IV to produce the compounds of formula Ia and Ib as illustrated for Examples 3 to 18 in Table II.

In general, the H$^1$ NMR spectra in DMSO-d$_6$ of the desired product exhibited a chemical shift for the 3-OH peak at about 9.5–9.8 δ and for the NH peak at about 12.2–12.6

TABLE II

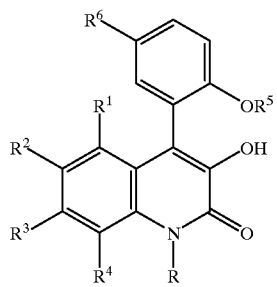

| Example No. | R | $R^1$ | $R^2$ | $R^3$ | $R^4$ | $R^5$ | $R^6$ | Melting Pt. | Yield (%) | Calculated (%) C; H; N | Found (%) C; H; N |
|---|---|---|---|---|---|---|---|---|---|---|---|
| 3 | H | H | $NO_2$ | H | H | $CH_3$ | Br | >330° C. | 92.1 | 49.13; 2.83; 7.16 | 48.97; 2.64; 7.07 |
| 4 | H | Cl | H | Cl | H | $CH_3$ | Br | 306–307 | 92.2 | 46.30; 2.43; 3.37 | 46.34; 2.36; 3.34 |
| 5 | H | H | H | Cl | H | $CH_3$ | Cl | 303–305 | 97.5 | 57.17; 3.30; 4.17 | 56.90; 3.35; 3.93 |
| 6 | H | H | H | H | H | H | Br | 220–221 | 95.8 | 54.24; 3.03; 4.22 | 53.85; 3.11; 4.11 |
| 7 | $CH_3$ | H | H | H | H | H | Br | 301–302 | 83.5 | 55.51; 3.49; 4.05 | 54.93; 3.37; 3.88 |
| 8 | H | H | H | H | H | H | Cl | 336–338 | 77.3 | 61.46; 3.65; 4.78 | 61.57; 3.48; 4.62 |
| 9 | H | H | $NO_2$ | H | H | H | Br | >330° C. | 96.0 | 47.09; 2.53; 7.32 | 47.09; 2.15; 7.02 |
| 10 | H | H | H | $CF_3$ | H | H | Cl | 224–225 | 92.3 | 52.17; 2.85; 3.80 | 52.07; 2.85; 3.77 |
| 11 | H | H | H | $CF_3$ | H | H | Br | 182 dec | 92.8 | 46.55; 2.54; 3.29 | 46.56; 2.48; 3.31 |
| 12 | H | Cl | Cl | H | H | H | Br | 292 dec | 95.6 | 43.93; 2.21; 3.42 | 43.97; 2.08; 3.30 |
| 13 | H | H | Cl | H | H | H | Cl | >335° C. | 93.0 | 54.70; 3.00; 4.25 | 54.63; 2.73; 4.10 |
| 14 | H | Cl | H | H | H | H | Cl | 295–297 | 90.4 | 55.31; 2.91; 4.30 | 55.27; 2.66; 4.19 |
| 15 | H | H | H | Cl | H | H | Cl | 281–283 | 93.1 | 54.11; 3.09; 4.21 | 53.90; 2.72; 4.13 |
| 16 | H | H | $CF_3$ | H | H | H | Cl | 313–315 | 66.9 | 54.03; 2.55; 3.94 | 53.86; 2.24; 3.72 |
| 17 | H | H | $CF_3$ | H | H | H | Br | 308–310 | 84.7 | 48.03; 2.27; 3.50 | 47.61; 2.52; 3.29 |
| 18 | $CH_3$ | Cl | H | Cl | H | H | Cl | 265–267 | 82.6 | 51.85; 2.72; 3.78 | 51.69; 2.63; 3.43 |

EXAMPLES 19–21

Following the general procedures Nos. 1, 2 and 3, wherein $R^a$ is $CH_2OCH_3$, and the representative Examples 1 and 2, the following 4-aryl-3-hydroxyquinolin-2-one products are made using the appropriate intermediates of formulas III and IV to produce the compounds of formula I*b* as illustrated for Examples 19 to 21 in Table Ill.

TABLE III

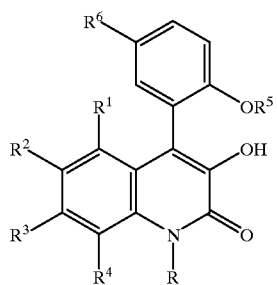

| Example No. | R | $R^1$ | $R^2$ | $R^3$ | $R^4$ | $R^5$ | $R^6$ | Melting Pt. | Yield (%) | Calculated (%) C; H; N | Found (%) C; H; N |
|---|---|---|---|---|---|---|---|---|---|---|---|
| 19 | H | H | Br | H | H | H | Br | >330° C. | 93.1 | 43.08; 2.36; 3.35 | 43.08; 2.03; 3.28 |
| 20 | H | H | Br | H | H | H | Cl | >330° C. | 75.4 | 49.15; 2.47; 3.82 | 49.08; 2.56; 3.64 |
| 21 | H | H | H | H | Cl | H | Cl | 286–288 | 90.1 | 54.41; 3.04; 4.23 | 54.54; 2.96; 4.02 |

What is claimed is:

1. A method for the treatment of disorders responsive to opening of the large conductance calcium-activated potassium channels in a mammal in need thereof, which comprises administering to said mammal a therapeutically effective amount of a compound of the formula

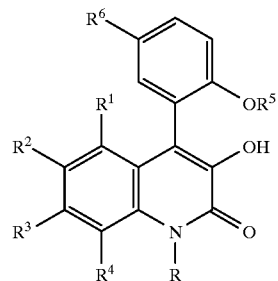

wherein
R is hydrogen or methyl;
$R^1$, $R^2$, $R^3$ and $R^4$ each are independently hydrogen, bromo, chloro or trifluoromethyl, and
when $R^1$, $R^3$ and $R^4$ are hydrogen, $R^2$ is nitro with the proviso that $R^1$, $R^2$, $R^3$ and $R^4$ are not all hydrogen;
$R^5$ is hydrogen or methyl; and
$R^6$ is bromo or chloro;

or a nontoxic pharmaceutically acceptable salt thereof.

2. The method of claim 1 wherein the compound is selected from the group consisting of:

5,7-dichloro-4-(5-chloro-2-hydroxyphenyl)-3-hydroxy-2(1H)-quinolinone;

6-nitro-4-(5-bromo-2-hydroxyphenyl)-3-hydroxy-2(1H)-quinolinone;

7-trifluoromethy-4-(5bromo-2-hydroxyphenyl)-3-hydroxy-2(1H)-quinolinone;

5,7-dichloro-4-(5-bromo-2-hydroxyphenyl)-3-hydroxy-2(1H)-quinolinone;

6-bromo-4-(5-bromo-2-hydroxyphenyl)-3-hydroxy-2(1H)-quinolinone;

6-bromo-4-(5-chloro-2-hydroxyphenyl)-3-hydroxy-2(1H)-quinolinone;

6-trifluoromethyl-4-(5-chloro-2-hydroxyphenyl)-3-hydroxy-2(1H)-quinolinone; and 6-trifluoromethyl-4-(5-bromo-2-hydroxyphenyl)-3-hydroxy-2(1H)-quinolinone.

* * * * *